US008462678B2

(12) United States Patent
Splinter et al.

(10) Patent No.: US 8,462,678 B2
(45) Date of Patent: Jun. 11, 2013

(54) SYSTEM AND METHOD FOR OPERATING A WIRELESS MEDICAL DEVICE INTERROGATION NETWORK

(75) Inventors: Tim John Splinter, Vadnais Heights, MN (US); Kenneth P. Hoyme, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1574 days.

(21) Appl. No.: 11/593,854

(22) Filed: Nov. 6, 2006

(65) Prior Publication Data

US 2008/0109051 A1    May 8, 2008

(51) Int. Cl.
*H04B 7/00*    (2006.01)
(52) U.S. Cl.
USPC ........................................ 370/310
(58) Field of Classification Search
USPC ................ 370/310; 607/60, 59; 340/539.12
See application file for complete search history.

(56) References Cited

U.S. PATENT DOCUMENTS

| | | | |
|---|---|---|---|
| 6,024,699 A | 2/2000 | Surwit et al. | |
| 6,083,248 A | 7/2000 | Thompson | |
| 6,168,563 B1 | 1/2001 | Brown | |
| 6,171,256 B1 | 1/2001 | Joo et al. | |
| 6,203,495 B1 | 3/2001 | Bardy | |
| 6,221,011 B1 | 4/2001 | Bardy | |
| 6,312,378 B1 | 11/2001 | Bardy | |
| 6,416,471 B1 | 7/2002 | Kumar et al. | |
| 6,827,670 B1 | 12/2004 | Stark et al. | |
| 7,027,872 B2 | 4/2006 | Thompson | |
| 7,060,031 B2 | 6/2006 | Webb et al. | |
| 2002/0013614 A1* | 1/2002 | Thompson | 607/60 |
| 2002/0098840 A1* | 7/2002 | Hanson et al. | 455/435 |
| 2003/0004403 A1* | 1/2003 | Drinan et al. | 600/301 |
| 2003/0088295 A1* | 5/2003 | Cox | 607/60 |
| 2004/0023651 A1* | 2/2004 | Gollnick et al. | 455/423 |
| 2004/0103001 A1 | 5/2004 | Mazar et al. | |
| 2005/0110654 A1* | 5/2005 | Kitano et al. | 340/825.72 |
| 2006/0066449 A1* | 3/2006 | Johnson | 340/539.12 |
| 2006/0121846 A1* | 6/2006 | Mazar et al. | 455/7 |
| 2006/0253300 A1 | 11/2006 | Somberg et al. | |
| 2007/0135855 A1* | 6/2007 | Foshee et al. | 607/31 |

FOREIGN PATENT DOCUMENTS

WO    WO 2006/01124    * 2/2006

OTHER PUBLICATIONS

Health Insurance Portability and Accountability Act of 1996, Pub. L. No. 104-191, 110 Stat. 1936 (Aug. 21, 1996).
E. Hammond, "National Committee on Vital and Health Statistics, Subcommittee on Health Data Needs, Standards and Security," http://www.ncvhs.hhs.gov/970211t3.htm, pp. 1-4 (Feb. 11, 1997).

(Continued)

*Primary Examiner* — Melody Mehrpour
(74) *Attorney, Agent, or Firm* — Pauly, DeVries, Smith & Deffner LLC

(57) ABSTRACT

A system and method for operating a wireless medical device interrogation network is provided. Data exchange sessions are transacted with a wireless medical device over a plurality of interrogation points that each cover different zones of interrogation. State regarding interim data packets exchanged during each data exchange session is maintained and is accessible by each of the interrogation points. Frequency agile switching between the interrogation points and the wireless medical device during a wireless data exchange session is supported.

25 Claims, 8 Drawing Sheets

OTHER PUBLICATIONS

Security and Electronics Signature Standards; Proposed Rule, Federal Register, vol. 63, No. 155 (Aug. 12, 1998).

W. Diffie, "The First Ten Years of Public-Key Cryptography," Proceedings of the IEEE, vol. 76, No. 5, pp. 560-577 (May 1988).

File History of Co-pending U.S. Appl. No. 11/122,593, "System and Method for Managing Patient Triage in an Automated Patient Management System," (196 pages).

* cited by examiner

SYSTEM AND METHOD FOR OPERATING A WIRELESS MEDICAL DEVICE INTERROGATION NETWORK

FIELD OF THE INVENTION

The invention relates in general to medical device interrogation and, specifically, to a system and method for operating a wireless medical device interrogation network.

BACKGROUND OF THE INVENTION

Remote patient management enables clinicians to follow patient well being without the presence or assistance of medical personnel. Homecare patient management devices, such as communicators or repeaters, collect and forward patient data over a data communications network, such as the Internet, to allow patient well being to be continually monitored and centrally analyzed.

Homecare patient management devices supplement conventional in-clinic programmers used to interrogate patient medical devices, which can include both implantable and external medical devices. Wireless personal patient management devices allow at-home, non-clinical retrieval of patient data through radio frequency interrogation through Bluetooth-compliant, WiFi-compliant, WiMax-compliant, and proprietary wireless communications.

RF interrogation replaces inductive telemetry for implantable medical devices (IMDs) and wired connections for external medical devices (EMDs). Radio frequency-capable (RF) patient management devices, including both homecare patient management devices and advanced programmers for clinical and institutional use, are used to perform RF interrogation of wireless patient medical devices. RF interrogation provided by each such device has a finite and limited signal range, which requires patients to stay physically within range of their patient management devices, particularly for implantable patient medical devices. The limited range can hinder interrogation sessions. In the less formal setting of a home, for instance, a patient might be tempted to move or otherwise inadvertently pass outside the range of a homecare patient management device, thereby interrupting the data exchange session. Moreover, some types of IMDs are designed to preserve battery life by pulsing and modulating bidirectional transaction signal power to the lowest level necessary to successfully transact a data exchange session, so even minor movement can potentially affect the session. Conversely, EMDs need only be close enough to communicate with a patient management device and are generally free of the RF transmission constraints and power management considerations of IMDs.

Other factors can further complicate interrogation sessions. RF interrogation is also susceptible to interference from external sources and environmental factors, such as household appliances or physical obstruction, which can cause a transient break or degradation in transmission signal. Moreover, homecare patient management devices are frequently installed on a bed stand or in a bathroom, which might be inconvenient or unavailable at times when interrogation sessions are scheduled or required, such as in response to caregiver instructions. Thus, reliance on a single interrogation point can cause frustration, particularly if the patient must continually search for an interference-free location within his or her home, or risk missing an interrogation session.

Conventional RF patient management devices generally offer only a single "zone" of interrogation within which the patient and each patient medical device must be physically situated during data exchange sessions. The physical constraint of a single interrogation zone requires physical proximity and near ideal RF conditions. Furthermore, interrupted data exchange sessions must either be rescheduled, or patient data could be lost or not timely relayed to the responsible clinician for proper assessment and action.

U.S. Pat. No. 7,060,031, issued Jun. 13, 2006 to Webb at al. discloses a method and apparatus for remotely programming IMDs. Caregivers generate IMD programming requests at programmers that are remotely connected to a server. The server is securely connected to a remote monitor, which transmits the programming requests to the IMDs through an antenna coupled via a physical connection or wireless telemetry. A plurality of remote monitors and antennas can be connected to the server, which provide multiple devices from which programming requests can be transmitted to an IMD from a single programmer. However, the Webb reference fails to disclose ensuring resilient handoff between physically independent and intelligent antennas that include safeguards against interference or programming session interruptions.

Therefore, there is a need for a user transparent extension to RF interrogation range constraints for remote patient care data exchange. Preferably, such an approach would provide a plurality of interrogation points within a homecare or clinical setting, or other environment, and would support automatic recovery of interrupted sessions with minimal affect on patient actions or privacy.

SUMMARY OF THE INVENTION

A wireless medical device interrogation network is provided through a patient management device, such as a homecare communicator or repeater, or clinical advanced programmer, that is interconnected with one or more antenna points, which together define a plurality of zones of interrogation. Data exchange sessions with patient medical devices are initiated by the patient management device or programmer, which designates an initial interrogation point by selecting one of the antenna points or itself. The initial interrogation point enables wandless startup, that is, the automatic initiation of an interrogation session through long range RF, as opposed to short range inductive, telemetry. Each patient medical device is wirelessly interrogated through the designated interrogation point through which patient data can be uploaded and, in a further embodiment, programming instructions downloaded. The antenna points and the patient management device maintain state, which chronicles and tracks the progress of the data exchange session and provides a resumption point, should the session be interrupted or subject to interference. The antenna points and the patient management device automatically perform a transfer of control to a new interrogation point upon sensing an interruption to seamlessly resume the session, if, for example, the patient moves about or interference is encountered from an external source or environmental factor, such as a household appliance or physical obstruction. Upon the successful completion of the data exchange session, a final data set is consolidated and provided to a centralized server or other external system or data repository. Where data exchange sessions are transacted with multiple patient medical devices, patient data and programming instructions are respectively assembled or applied for each specific patient and patient medical device.

One embodiment provides a system and a method for operating a wireless medical device interrogation network. Data exchange sessions are transacted with a wireless medical device over a plurality of interrogation points that each cover different zones of interrogation. State regarding interim data packets exchanged during each data exchange session is maintained and is accessible by each of the interrogation points. Frequency agile switching between the interrogation points and the wireless medical device during a wireless data exchange session is supported. The interrogation points could each have one or more antennas, which define or expand their respective zones of interrogation.

A further embodiment provides a storage medium holding computer-readable code and a method for implementing a wireless medical device interrogation protocol. A wireless data exchange session is transacted. Distinct frequency agile connections are provided with a wireless medical device through a plurality of interoperative interrogation points. Data is exchanged between the wireless medical device and the interrogation points over the distinct frequency agile connections. Control is transferred over the wireless data exchange session. An interruption in the wireless data exchange session is sensed and the interrogation point proximal to the wireless medical device is designated. The wireless data exchange session with the wireless medical device is automatically resumed on the designated interrogation point.

A still further embodiment provides a wireless antenna point for use in a medical device interrogation network. A device interface wirelessly connects the wireless antenna point to a medical device. A buffer stages data exchanged with the medical device. State is maintained to track the data last successfully exchanged. A network interface connect the wireless antenna point with one or more of other wireless antenna points and a patient management device.

Still other embodiments will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Automated Patient Management Environment

Figure 1:
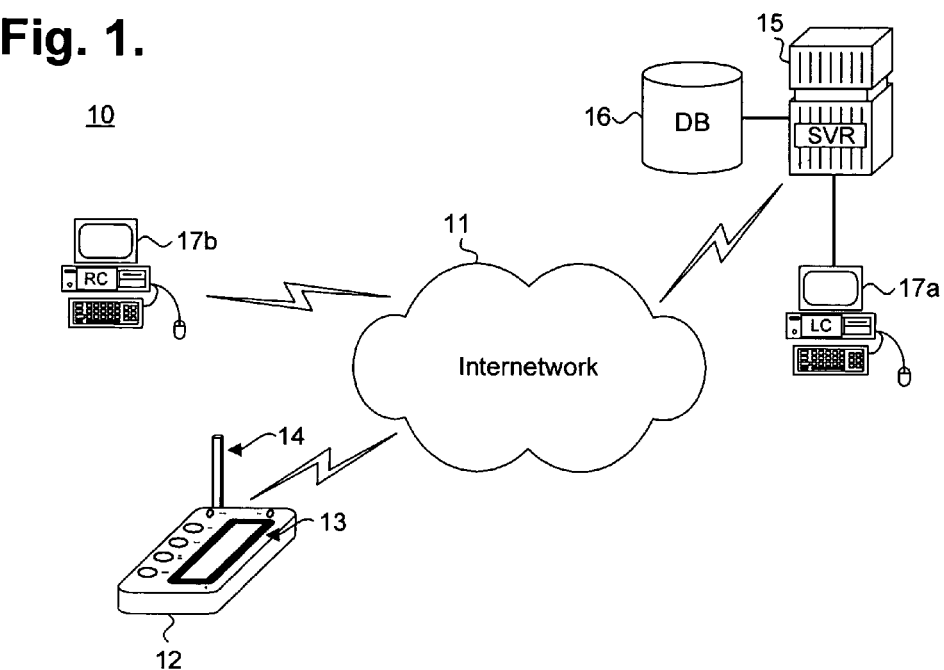
FIG. 1 is a functional block diagram showing, by way of example, an automated patient management environment.

Automated patient management encompasses a range of activities, including remote patient management and automated monitoring and diagnosis of patient health, such as described in commonly-assigned U.S. Patent application Pub. No. US2004/0103001, published May 27, 2004, pending, the disclosure of which is incorporated by reference. FIG. 1 is a functional block diagram showing, by way of example, an automated patient management environment 10. A patient management device 12 is installed in a patient's home or in a clinical or hospital environment to provide automated patient management through wireless interrogation of patient medical devices. An advanced RF telemetry-capable programmer could also be used in a clinical or hospital environment. Additionally, other environments are possible.

Wireless interrogation of patient medical devices should only be performed with the knowledge and permission of the patient. The permission can be either obtained as an implicit condition of receiving an RF-capable patient medical device, or as express permission affirmatively granted by the patient. Providing proper patient disclosure and release before engaging in wireless interrogation sessions should help allay personal privacy concerns, for instance, whereabouts tracking and activities monitoring, which may present as an artifact of wireless interconnectivity.

Homecare patient management devices include repeaters and communicators, and institutional patient management devices include RF-capable advanced programmers that can perform wireless interrogation. The patient management device 12 is remotely interconnected to a centralized server 15 over an internetwork 11, such as the Internet, or through a public telephone exchange (not shown), such as a conventional or mobile telephone network. Other patient monitoring or communications devices are possible. In addition, the internetwork 11 can provide both conventional wired and wireless interconnectivity. In one embodiment, the internetwork 11 is based on the Transmission Control Protocol/Internet Protocol (TCP/IP) network communication specification, although other types or combination of networking implementations are possible. Similarly, other network topologies and arrangements are possible.

Each patient management device 12 includes a user interface 13 that can be operated by the patient, or his or her attendant, and a wireless transceiver 14, which provides wireless access to patient medical devices using wireless telemetry based on, for example, "strong" Bluetooth, IEEE 802.11 wireless fidelity "WiFi" and "WiMax," and other radio frequency (RF) interfacing standards. Other types and configurations of patient data source interfacing are possible. Patient management devices 12, along with dedicated antenna points, form wireless medical device interrogation networks through which patient medical devices are accessed, as further described below with reference to FIGS. 2-5. Both the patient management device 12 and antenna points serve as an interrogation point to which a patient medical device can connect and be interrogated. The antenna points extend the area of physical wireless coverage by forming interrogation zones that supplement the area covered by each patient management device 12. A patient is able to move freely about during an interrogation session without risk of causing an interruption or interference, or to be inconvenienced by having only a single access point on the patient management device 12.

Patient medical devices include monitoring, diagnostic, and therapeutic medical devices, which can be implantable or external. The medical devices collect and forward patient data either as a primary or supplemental function. The patient medical devices collect quantitative objective physiological measures on a substantially continuous or scheduled basis and also record the occurrence of events, such as therapy or irregular physiometric readings. In a further embodiment, the patient management device 12 or other ancillary system, such as a personal computer, records or communicates qualitative subjective quality of life (QOL) measures that reflect the personal impression of physical well-being perceived by the patient at a particular time. Patient data includes physiological measures, which can be quantitative or qualitative, parametric data regarding the status and operational characteristics of the patient medical device itself, and environmental parameters, such as the temperature or time of day. In a further embodiment, patient data can be directly entered by a patient. For example, answers to health questions can be input into the patient management device 12 through the user interface 13 or through an ancillary system. Other types of patient data are possible.

In a further embodiment, the collected patient data can also be accessed and analyzed by one or more clients, either locally configured systems 17a directly interfaced to the centralized server 15 or remotely-interconnected systems 17b available over the internetwork 11. The clients systems 17a-b can be used, for example, by clinicians to securely access stored patient data assembled in a database 16 coupled to the centralized server 15 and to select and prioritize patients for health care provisioning, such as respectively described in commonly-assigned U.S. patent application, Ser. No. 11/121,593, filed May 3, 2005, pending, and U.S. patent application, Ser. No. 11/121,594, filed May 3, 2005, pending, the disclosures of which are incorporated by reference. Although described herein with reference to physicians or clinicians, the entire discussion applies equally to organizations, including hospitals, clinics, and laboratories, and other individuals or interests, such as researchers, scientists, universities, and governmental agencies, seeking access to the patient data.

In a still further embodiment, patient medical devices can be remotely programmed through the patient management device 12. The patient management device 12 receives programming instructions from the centralized server 15, which, following authentication and integrity checking, are applied to the patient medical device. Programming instructions could also originate from the patient management device 12 itself or in combination with the centralized server 15 or other external sources.

In a further embodiment, patient data is safeguarded against unauthorized disclosure to third parties, including during collection, assembly, evaluation, transmission, and storage, to protect patient privacy and comply with recently enacted medical information privacy laws, such as the Health Insurance Portability and Accountability Act (HIPAA) and the European Privacy Directive. At a minimum, patient health information that identifies a particular individual with health- and medical-related information is treated as protectable, although other types of sensitive information in addition to or in lieu of specific patient health information could also be protectable.

In a further embodiment, multiple patients and patient medical devices can be wirelessly interrogated by commonly shared patient management devices 12 or advanced programmers. To ensure security and patient privacy, patient data, and in a further embodiment, programming instructions, include a patient medical device identifier that ensures correct authentication and positive patient identification.

Preferably, the server 15 is a server-grade computing platform configured as a uni-, multi- or distributed processing system, and the client systems 17a-b are general-purpose computing workstations, such as a personal desktop or notebook computer. In addition, the patient management device 12, server 15, and client systems 17a-b are programmable computing devices that respectively execute software programs and include components conventionally found in computing device, such as, for example, a central processing unit (CPU), memory, network interface, persistent storage, and various components for interconnecting these components. Other systems and components are possible.

Wireless Medical Device Interrogation Networks

Each patient management device 12 provides a single access point for interfacing to patient medical devices through RF telemetry. The maximum wireless service range of a patient management device 12 is physically limited by the capabilities of the wireless transceiver and antenna provided. The effective range can also be affected by external sources and environmental factors, such as interference from household appliances or physical obstructions, which can both decrease the physical range and cause "dead" spots within which poor or nonexistent signal quality is experienced. Consequently, a patient must generally remain within the effective communications range of the patient management device throughout an interrogation session and should preferably refrain from moving about to avoid causing a lapse in communications.

The effective range of patient management devices 12 can be extended by building a network of wireless access or interrogation points that provide wandless startup and multiple frequency agile interfaces to patient medical devices within a physical environment, such as a patient's home, medical clinic or hospital, or adult care or nursing facility. Within the network, each patient management device 12 serves as both a centralized hub for consolidating data from all interrogation points and for communicating with external devices through a network gateway or portal. In addition, the status of on-going sessions is tracked through state that is accessible from all interrogation points to enable automatic hand-off and recovery, should a switchover between the interrogation points become necessary due to, for instance, patient movement.

One-to-One Interrogation Networks

Figure 2:
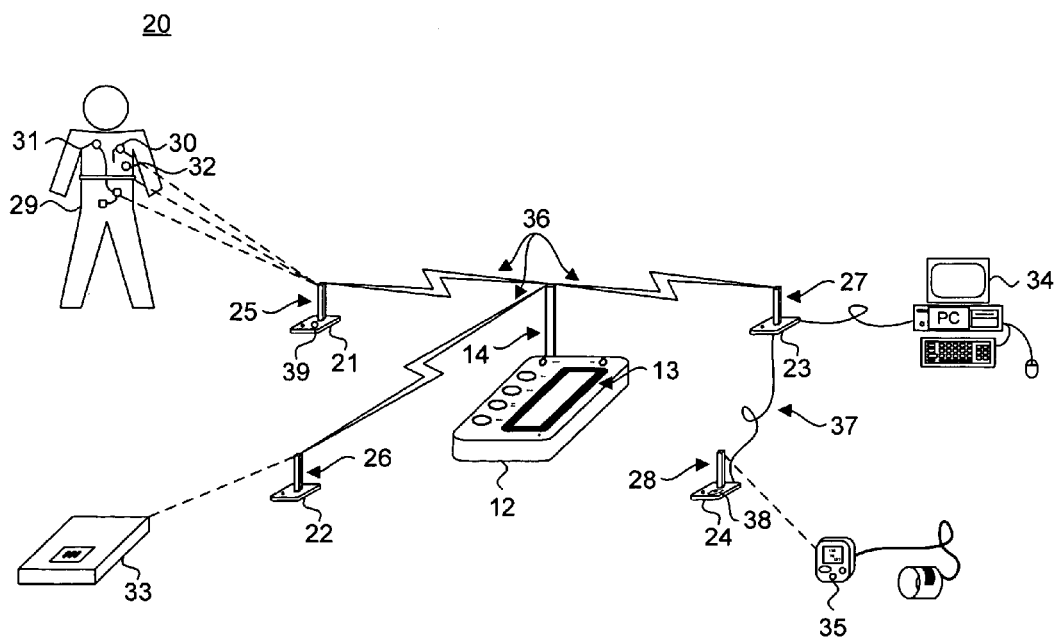
FIG. 2 is a functional block diagram showing, by way of example, a wireless medical device interrogation network organized in a one-to-one pairing.

In basic form, a single wireless medical device interrogation network 20 is paired with just one patient 29, who may have one or more patient medical devices 30-33. FIG. 2 is a functional block diagram showing, by way of example, a wireless medical device interrogation network 20 organized in a one-to-one pairing. The wireless medical device interrogation network 20 provides multiple wireless access or interrogation points, which include at least one patient management device 12 and one or more antenna points 21-24. Each antenna point 21 provides an interrogation point that covers a different physical zone within the operating environment in addition to the physical zone covered by the patient management device 12, as further described below with reference to FIG. 6. The multiple interrogation points allow a patient 29 to move freely about during a data exchange session without risk of causing an interruption to or interference with the session, or to be limited or inconvenienced by having only the single interrogation point provided by the patient management device 12.

The antenna points 21-24 and the patient management device 12 each create a wireless interrogation zone that may overlap or be completely discrete from other wireless interrogation zones in the network 20. The interrogation zones logically define physical areas of wireless coverage within which patient medical devices 21-24 can be wirelessly interrogated. For instance, a wireless interrogation zone could be provided in a downstairs living room and another zone in an upstairs master bedroom with little to no wireless coverage in between. Wireless interrogation zones could also be located next to each other to provide an extended wireless interrogation zone, such as might be provided in an elder care facility. Other wireless interrogation zone arrangements and topologies are possible.

The devices 12, 21-24 collectively enable wandless startup and perform frequency agile switching to transparently transfer control between the individual interrogation zones. Each antenna point 21-24 includes at least one wireless transceiver and antenna 25-28 that forms a wireless interrogation zone, although both the patient management device 12 and the antenna points 21-24 can have multiple wireless transceivers and antennas to further define or increase the zones of wireless coverage that each provide.

Both the patient management device 12 and the antenna points 21-24 interface to patient medical devices, which include, by way of example, medical therapy devices that deliver or provide therapy to the patient 29, medical sensors that sense patient physiometry, and measurement devices for collecting environmental and other data occurring independent of the patient 29. Each medical device can generate one or more types of patient data and can incorporate components for delivering therapy, sensing physiological data, measuring environmental parameters, or provide a combination of functionality. Medical therapy devices include implantable medical devices (IMDs) 30, such as pacemakers, implantable cardiac defibrillators (ICDs), drug pumps, and neurostimulators, and external medical devices (EMDs) 31. Medical sensors include implantable sensors 32, such as implantable heart and respiratory monitors and diagnostic multi-sensor non-therapeutic devices, and external sensors 33, 35, such as thermometers, heart rate monitors, Holter monitors, Spirometers, weight scales 33, and blood pressure cuffs 35. External medical devices and sensors can operate autonomously or under patient, attendant, or caregiver control, and can include a user interface for receiving or providing subjective patient feedback or communications.

Figure 7:
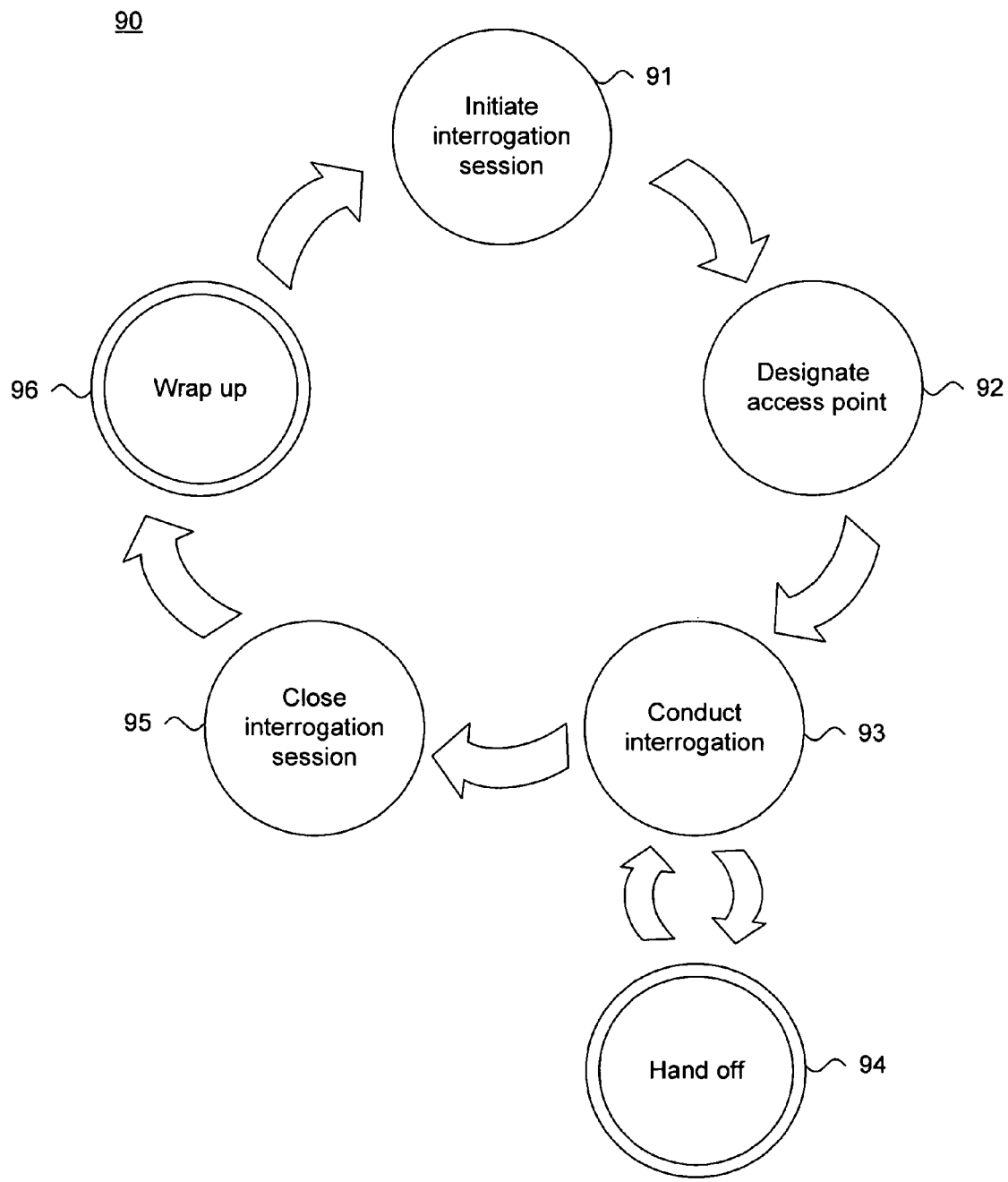
FIG. 7 is a process flow diagram showing a method for operating a wireless medical device interrogation network, in accordance with one embodiment.

Generally, the patient management device 12 initiates each data exchange session by polling one or more of the patient medical devices, as further described below with reference to FIG. 7. In a further embodiment, data exchange sessions can be scheduled to start upon the initiative of the patient medical devices or on demand by the patient 29, attendant, caregiver, or other external source. Other forms of data exchange session initiation are possible.

During each data exchange session, the patient medical device must be within at least one wireless interrogation zone. The designated antenna point 21-24 or the patient management device 12 wirelessly communicates with the activated patient medical device through their respective wireless transceiver 25-28 and 36. Patient data uploaded from the patient medical devices is temporarily buffered by the interrogating device and is consolidated into a final data set for the patient upon the successful completion of the data exchange session, as further described below with reference to FIG. 11. Generally, the patient management device 12 performs the assembly and consolidation of the interim patient data, although an antenna point 21-24 or other device could also perform assembly and consolidation.

Figure 8:
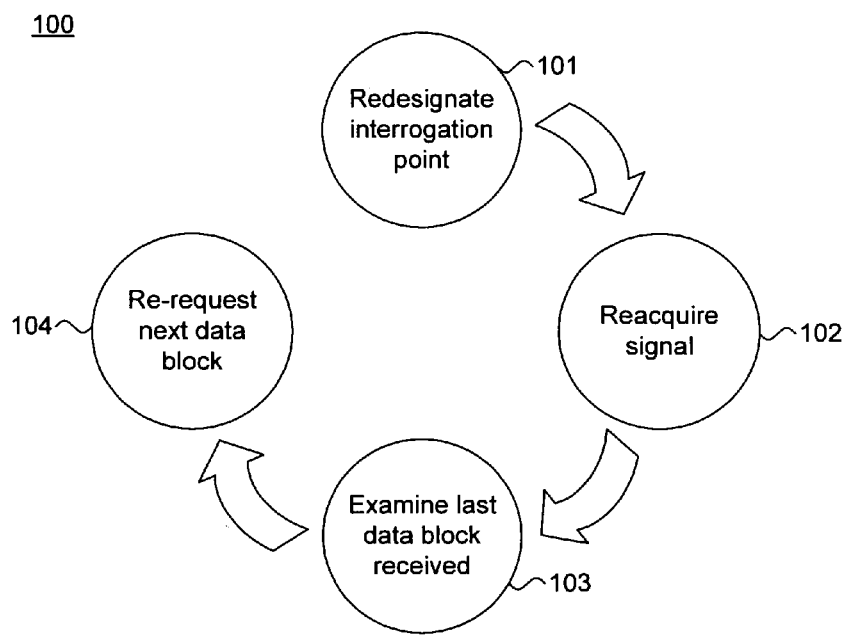
FIG. 8 is a process flow diagram showing medical device hand-off in the wireless medical device interrogation network of FIG. 2.

During each data exchange session, the antenna points 21-24 and the patient management device 12 monitor session progress and maintain state that set a resumption point, should the data exchange session be interrupted, as further described below with reference to FIG. 8. In a further embodiment, the state is maintained by the patient medical device, which tracks the data sets that have been successfully uploaded to avoid performing a duplicate upload of data already sent and to enable the patient medical device to free storage space for other patient data. Generally, the state includes the last packet of interim data exchanged with the patient medical device and can include a sequence number or other packet identifier. In a further embodiment, the antenna points 21-24 and the patient management device 12 can download programming instructions into the patient medical device, which can be reflected on a programming status indicator 39 or other indication on an antenna point 21-24 and the user interface 13 of the patient management device 12.

The antenna points 21-24 can be interconnected to a central hub, which is typically the patient management device 12. The antenna points 21-24 can also be interconnected in series or relay. Other configurations and topologies are possible. Additionally, the antenna points 21-24 can intercommunicate with each other and with the patient medical device 12 either through wireless signals 36 or via a wired connection 37. Other forms of medical device interrogation and network interfacing are possible.

In a still further embodiment, the antenna points 21-24 and the patient management device 12 can interface to a personal computer 34 or other general purpose computing device, which can be used to collect both quantitative and qualitative data from the patient, including QOL measures, such as described in commonly-assigned U.S. Pat. No. 6,221,011 issued Apr. 24, 2001, the disclosure of which is incorporated by reference. Similarly, the antenna points 21-24 can include sensors 38 to provide external monitoring of patient physiometry and other data. Finally, the patient medical device 12 can perform diagnoses and feedback locally to a patient 29, such as described in commonly-assigned U.S. Pat. No. 6,312,378 issued Nov. 6, 2001, and U.S. Pat. No. 6,203,495 issued Mar. 20, 2001, the disclosures of which are incorporated by reference. Other types of antenna point and patient medical device functionality are possible.

One-to-Many Interrogation Networks

Figure 3:
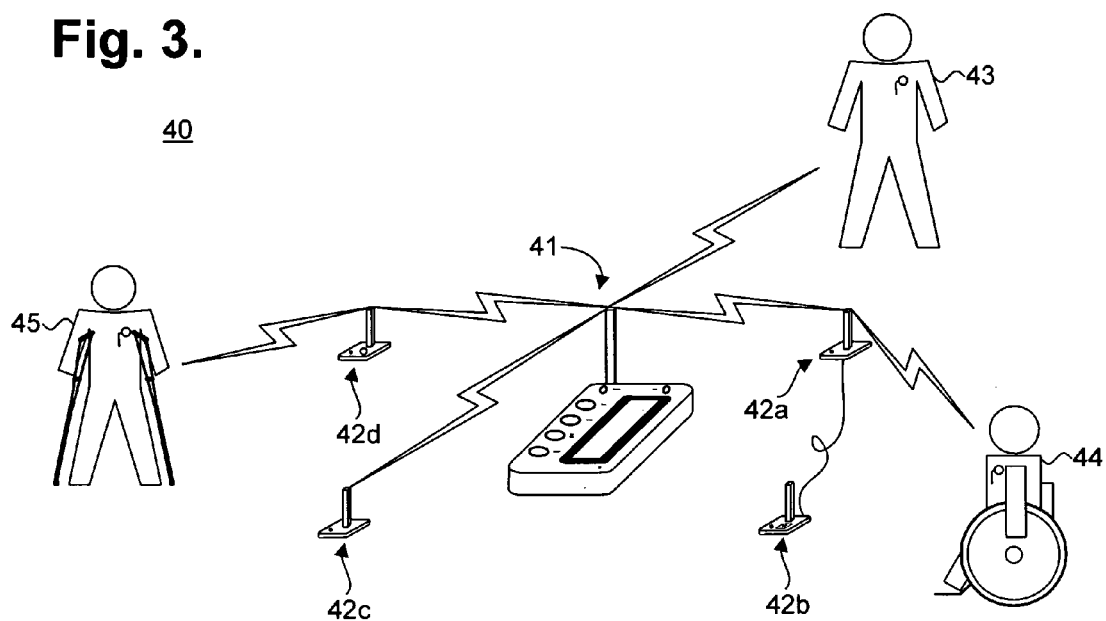
FIG. 3 is a functional block diagram showing, by way of example, a wireless medical device interrogation network organized in a one-to-many pairing.

In extended form, additional interrogation networks and patient medical devices can be combined into expanded topologies. For example, a single wireless medical device interrogation network can be paired with multiple patients and their patient medical devices, such as in a home environment where a single patient management device might be shared by several family members. FIG. 3 is a functional block diagram showing, by way of example, a wireless medical device interrogation network 40 organized in a one-to-many pairing. A single patient management device 41 serves as a centralized communications hub with at least one remotely coupled antenna point 42a-d. A plurality of patients 43-45, each of whom can have one or more patient medical devices, are uniquely identifiable by the patient management device 41, such as described in commonly-assigned U.S. patent application Ser. No. 11/301,214, filed Dec. 12, 2005, pending, the disclosure of which is incorporated by reference. Each patient 43-45 is able to participate in an interrogation session via the interrogation network 40, either individually or at the same time, through any of the interrogation points 41, 42a-d and the patient management device 41 consolidates individual data packets for analysis and forwarding to the centralized server 15, or other external system or data repository. The identifier associated with each patient management device is used to assemble the patient data belonging to each patient and patient management device, as further described below with reference to FIG. 11.

Many-to-One Interrogation Networks

Figure 4:
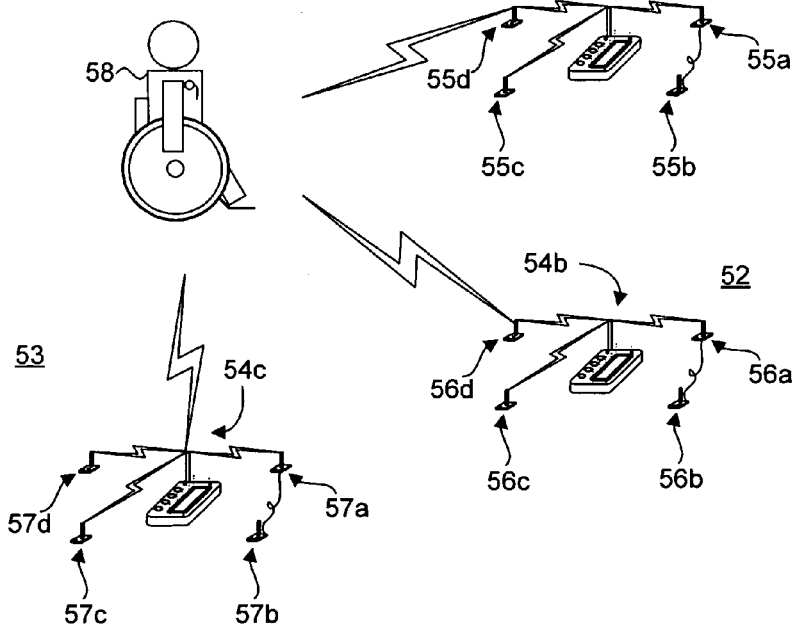
FIG. 4 is a functional block diagram showing, by way of example, a set of wireless medical device interrogation networks organized in a many-to-one pairing.

Conversely, multiple wireless medical device interrogation networks can be paired with a single patient and his or her patient medical devices, such as for a patient with a principal residence and a vacation home with dedicated interrogation networks deployed within each. FIG. 4 is a functional block diagram showing, by way of example, a set of wireless medical device interrogation networks 50 organized in a many-to-one pairing. A plurality of patient management devices 54a-c each form distinct interrogation networks 51, 52, 53 and serve as centralized communications hubs with at least one antenna point 55a-d, 56a-d, 57a-d remotely coupled. A single patient 58, who can have one or more patient medical devices, is uniquely identifiable by each patient management device 54a-c. The patient 58 is able to participate in an interrogation session via any of the interrogation networks 51, 52, 53 through any of the interrogation points 54a-c, 55a-d, 56a-d, 57a-d and each patient management device 54a-c consolidates individual data packets for analysis and forwarding to the centralized server 15, or other external system or data repository.

Many-to-Many Interrogation Networks

Health care environments, such as medical clinics or hospitals, and adult care or nursing facilities, frequently must be able to provide care for a population of patients throughout an environment that may extend over a physical area significantly larger than a personal residence. These environments are typically hostile to wireless signal exchange due to the plethora of electronic devices in operation at any time and the reinforced construction required of commercial facilities. Providing personalized RF-enabled patient management devices to interrogate each patient is economically infeasible and impractical, yet relying wholly on conventional wired devices, such as inductive telemetry programmers, severely limits patient mobility and device availability.

Figure 5:
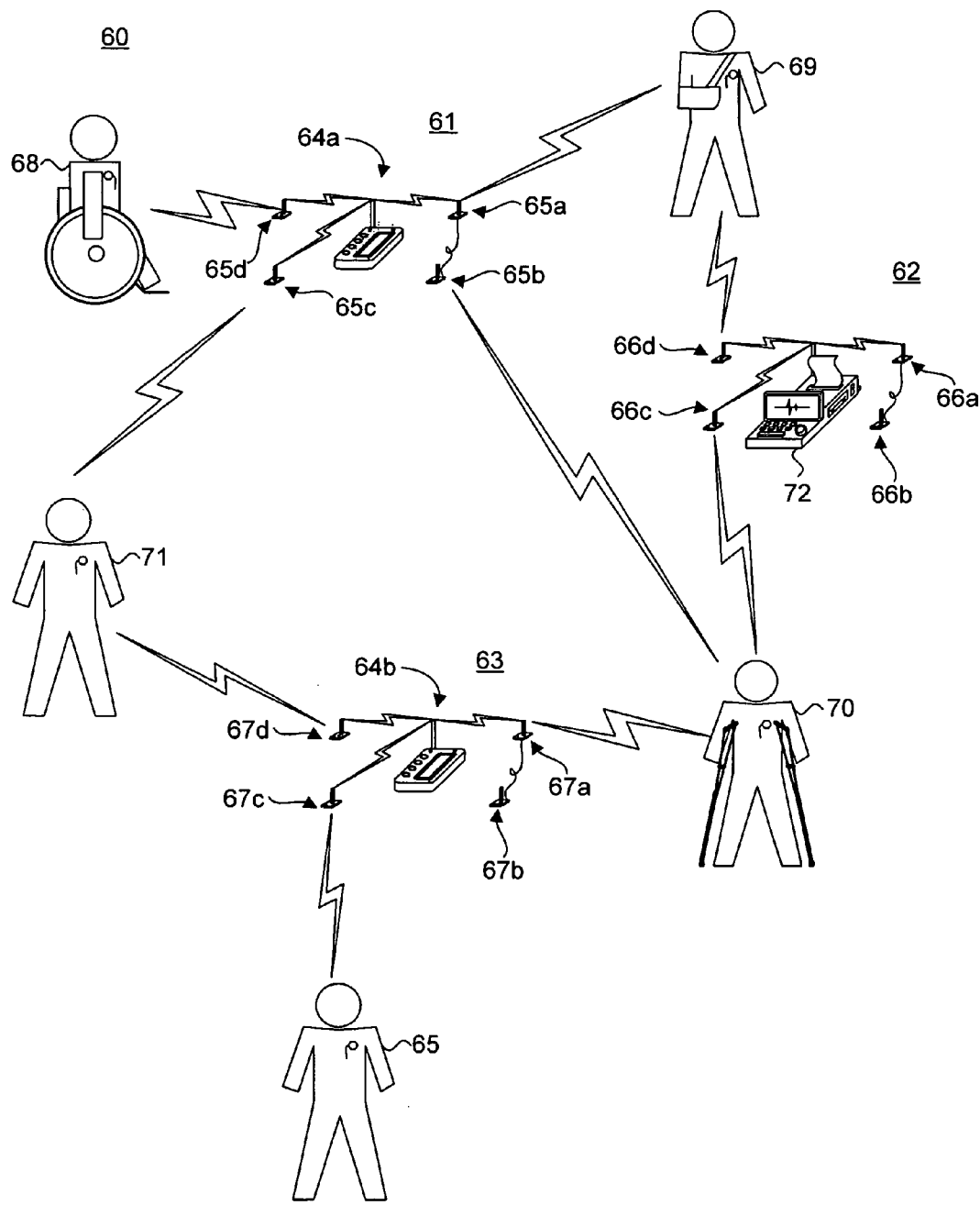
FIG. 5 is a functional block diagram showing, by way of example, a set of wireless medical device interrogation networks organized in a many-to-many pairing.

Alternatively, a series of logically interconnected wireless medical device interrogation networks can be paired with multiple patients, patient medical devices, and advanced programmers to provide an expanded institutional interrogation network. FIG. 5 is a functional block diagram showing, by way of example, a set of wireless medical device interrogation networks 60 organized in a many-to-many pairing. A plurality of patient management devices 64a-b and advanced programmers 72 each form distinct interrogation networks 61, 62, 63 and serve as centralized communications hubs with at least one antenna point 65a-d, 66a-d, 67a-d remotely coupled. A plurality of patients 68-71, each of whom can have one or more patient medical devices, are uniquely identifiable by the patient management devices 64a-b through patient medical device identifiers. Each patient 68-71 is able to participate in an interrogation session via any of the interrogation network 61, 62, 63, either individually or at the same time, through any of the interrogation points 64a-b, 65a-d, 66a-d, 67a-d. Each patient management device 64a-b consolidates individual data packets, which are further consolidated by patient by either one of the patient management devices 64a-b or by the centralized server 15. The patient-consolidated packets are then provided for analysis and forwarding to the centralized server 15, or other external system or data repository. The identifier associated with each patient management device is used to assemble the patient data belonging to each patient and patient management device, as further described below with reference to FIG. 11.

Zones of Interrogation

Figure 6:
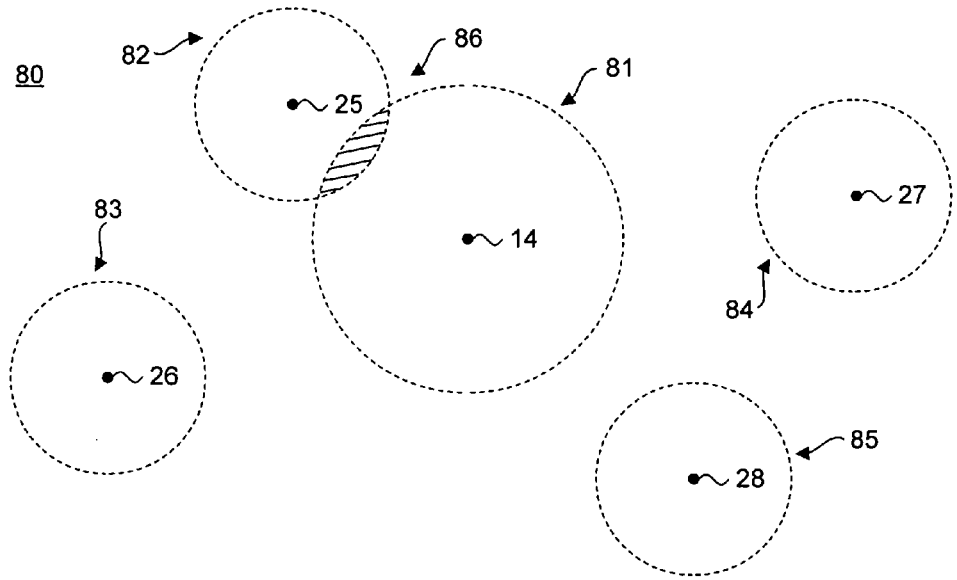
FIG. 6 is a functional block diagram showing, by way of example, zones of interrogation logically defined in the wireless medical device interrogation network of FIG. 2.

The zones of interrogation provided by the antenna points 21-24 and the patient management device 12 collectively form the wireless medical device interrogation network. FIG. 6 is a functional block diagram showing, by way of example, zones of interrogation 80 logically defined in the wireless medical device interrogation network 20 of FIG. 2. Each zone of interrogation 81-85 corresponds to the physical area of coverage provided by a single wireless transceiver 25-28 and 14 respectively operating on one of the antenna points 21-24 and the patient medical device 12. Each interrogation zone 81-85 covers a different area, but can overlap 36 or be entirely discrete from each other. The zones of interrogation 81-85 need not cover every physical part of the environment, such as a patient's home. Rather, the patient medical device 12 and antenna points 21-24 can be strategically placed throughout the environment to provide user friendly and convenient locations for wireless data exchange session.

Method Overview

Data exchange sessions are performed periodically with each of the patient medical devices to retrieve patient data that has been recorded or collected since the last interrogation and, in a further embodiment, to update programming instructions. FIG. 7 is a process flow diagram showing a method 90 for operating a wireless medical device interrogation network 20, in accordance with one embodiment. Data exchange sessions are the primary set of operations performed during an interrogation session between the patient medical devices and the network 20, although other operations are possible, including relaying information to the patient 29, resetting or remotely controlling patient medical devices, processing near real time alerts, and performing diagnostic and trouble-shooting operations.

Each interrogation session is initiated by the patient management device 12 through polling (operation 91). In a further embodiment, the interrogation sessions can be initiated by scheduling or on demand. The patient management device 12 serves as the network arbiter, which is responsible for designating the access point through which the data exchange session will initially be performed (operation 92). The access point, whether one of the antenna points 21-24 or the patient management device 12, can be selected based on any combination of factors, such as signal strength, physical location, priority, assigned order, and radio frequency. Other access point selection factors are possible.

The access point designated for interrogation conducts the interrogation of the selected patient medical device (operation 93), during which patient data can be received from and, in a further embodiment, programming instructions sent to the selected patient medical device. Each patient medical device is uniquely identified which, by extension, uniquely identifies the patient with whom the patient medical device is associated. For instance, a manufacturer's serial number can be used as a patient medical device identifier, as well as a randomly assigned number or other data. The identifier is included with each packet of patient data sent from and, in a further embodiment, programming instructions received by, a patient medical device. The identifier enables correct assembly of patient data in environments in which multiple patients of patient medical devices could participate either simultaneously or while patient data from another patient or device is still present in the network. The authenticity, integrity, and privacy of patient data can be assured by encryption and related cryptographic techniques.

A plurality of interrogation zones enables the patient 29 to move about freely and provide alternate wireless communications conduits, should the session be interrupted or suffer interference from an external source, such as a household appliance. The antenna points 21-24 and the patient management device 12 collectively perform a hand-off to transfer control, as necessary, to automatically resume an interrupted data exchange session (operation 94), as further described below with reference to FIG. 8. A hand-off is a frequency agile switch between interrogation points that enables the wireless medical device interrogation network 20 to provide resilience to interruptions and interference that might otherwise cause the session to abnormally terminate.

Figure 11:
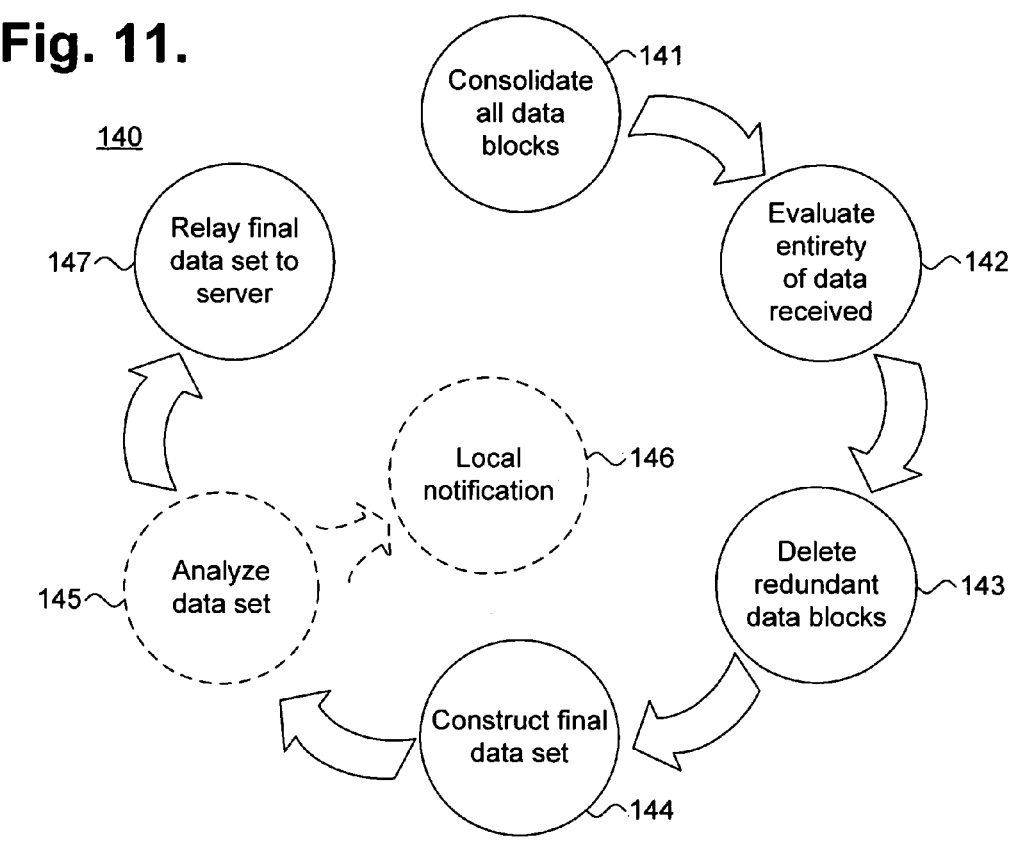
FIG. 11 is a process flow diagram showing data session wrap-up in the wireless medical device interrogation network of FIG. 2.

The interrogation session is closed upon the completion of the data exchange session (operation 95) and the patient management device 12, or other centrally designated device, including any of the antenna points 21-24, performs a wrap-up of the session (operation 96), as further described below with reference to FIG. 11. The wrap-up consolidates the data exchanged into a final data set, which can be forwarded to the centralized server 15 for further processing. The network 20 thereafter returns to a standby state pending initiation of a next interrogation session or other activity.

Medical Device Hand-Off

Data exchange sessions occur as one-to-one communications, which pair a patient medical device to a single interrogation point, which is either a patient management device or antenna point. One-to-many communications between a single patient medical device and multiple interrogation points are possible. However, contact between the patient medical device and the assigned interrogation point is susceptible to interruption or interference. An on-going data exchange session can nevertheless be continued by performing a hand-off operation. FIG. 8 is a process flow diagram 100 showing medical device hand-off in the wireless medical device interrogation network 20 of FIG. 2. A hand-off operation involves the patient medical device currently participating in a data exchange session and one or more of the interrogation points, which are either antenna points 21-24 or the patient medical device 12. The patient medical device 12 serves as the arbiter of the hand-off of interrogation point control, although any of the antenna points 21-24 could also control a hand-offhand-off. Other types of medical device hand-off are possible.

Initially, upon sensing an interruption or interference with the data exchange session, the patient management device 12 re-designates a substitute interrogation point based upon the same factors considered in designating the initial interrogation point, which include signal strength, physical location, priority, assigned order, and frequency (operation 101). Other interrogation point selection factors are possible. The re-designated interrogation point reacquires the wireless signal with the patient medical device (operation 102). Additionally, the re-designated interrogation point examines the last data block received successfully from the patient medical device and other state as needed (operation 103) to determine the point at which the data exchange session should be resumed. The state is accessible by each of the interrogation points and can include a sequence number assigned to each interim data packet received from the patient medical device. The next data block is thereafter re-requested from the patient medical device to resume the data exchange session and thereby complete the hand-off (operation 104).

Patient Data Upload

Figure 9:
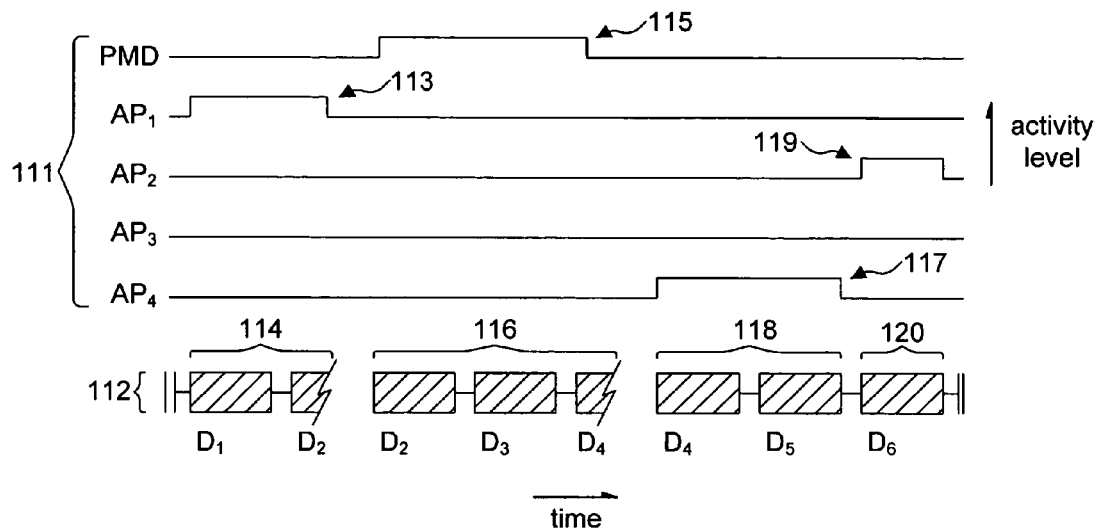
FIG. 9 is a timing diagram showing, by way of example, patient data upload during a wireless medical device interrogation session.

Data exchange sessions enable patient medical devices to upload patient data recorded or collected since the last interrogation. FIG. 9 is a timing diagram showing, by way of example, patient data upload 110 during a wireless medical device interrogation session. The x-axis represents time and the y-axis represents the activity level of each of the interrogation points 111. Interim data packets 112 represent the patient data being uploaded.

At the outset of the data exchange session, a first antenna point $AP_1$ is designated and becomes active 113, while receiving a first set of interim data packets 114. Although only one interrogation point 111 is active at any particular time throughout the data exchange session, each remaining interrogation point continually monitors the on-going session and maintains state to chronicle a resumption point, should the session be interrupted or suffer interference. The session is interrupted and the patient management device PMD is re-designated as the interrogation point. The patient management device PMD becomes active 115 and receives a second set of interim data packets 116, including a re-requested data packet that was incompletely received by the first antenna point $AP_1$. Again, the data exchange session is interrupted. A fourth antenna point $AP_4$ is re-designated as the interrogation point. The fourth antenna point $AP_4$ becomes active 117 and receives a third set of interim data packets 118. The data exchange session is again interrupted, but between the transmission of successive interim data packets. A second antenna point $AP_2$ is re-designated and becomes active 119 in time to receive the fourth and final set of interim data packets 120 without having to re-request patient data. The data exchange session then closes.

Programming Instruction Download

Figure 10:
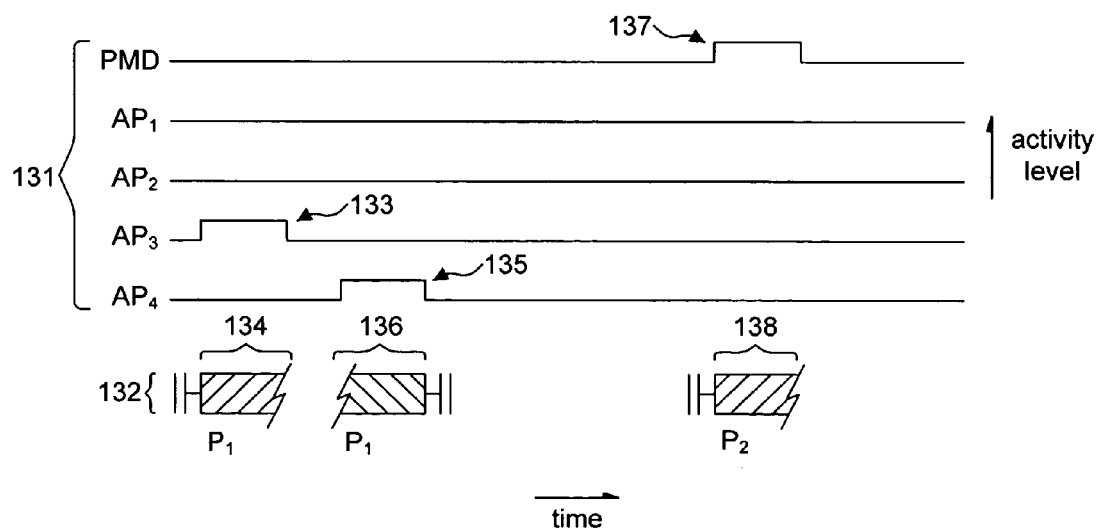
FIG. 10 is a timing diagram showing, by way of example, programming instruction download during a wireless medical device interrogation session.

In a further embodiment, patient medical devices can be remotely programmed through the wireless medical device interrogation network 20. FIG. 10 is a timing diagram showing, by way of example, programming instruction download 130 during a wireless medical device interrogation session. The x-axis represents time and the y-axis represents the activity level of each of the interrogation points 131. Programming patches 132 represent the programming instructions being downloaded.

Unlike patient data upload, the downloading of programming instructions must generally occur as a logically contiguous operation to avoid leaving the patient medical device in an inconsistent state, should the data exchange session terminate abnormally. Moreover, the programming of Class III medical devices is regulated and requires a certified control infrastructure. To ensure patient safety, if programming performed as part of a data exchange session is interrupted, such as by the patient moving out of range, the patient is generally prompted to resume the session, which will continue if the interruption has only been for a short duration. If the patient either ignores the prompt or the interruption becomes of long duration, the programming is halted and the earlier programming instructions on the patient medical device are recovered or restored to ensure a consistent state.

Initially, a third antenna point $AP_3$ is designated to perform programming instruction download and becomes active 133. However, only a portion of the programming instructions 134 are successfully downloaded, but a fourth antenna point $AP_4$ is re-designated and becomes active 135 in time to safely resume the programming by downloading the remaining portion of the programming instructions 136.

Later, a second set of programming instructions become available and the patient management device PMD is designated and becomes active 137. Only a portion of the programming instructions 138 are downloaded, after which the wireless medical device interrogation network 20 is unable to re-acquire a satisfactory interconnection with the patient medical device being programmed. Accordingly, the patient medical device automatically restores the previous set of programming instructions to recover a consistent state.

Data Session Wrap-Up

The interim patient data received by the antenna points 21-24 and the patient management device 12 must be consolidated into a final data set upon the successful completion of each data exchange session. FIG. 11 is a process flow diagram showing data session wrap-up 140 in the wireless medical device interrogation network 20 of FIG. 2. In a further embodiment, progressive sets of patient data can be formed without waiting for the completion of the entire data exchange session by only consolidating the interim patient data received within preset time intervals, or based on size, content, or other considerations. Other types of data session wrap-up are possible.

Each patient medical device is uniquely identified and the identifier is included as part of patient data and programming instructions to ensure proper authentication and positive identification of patients and their patient medical devices. Initially, the patient management device 12, or other centrally designated device, including any of the antenna points 21-24, consolidates all of the interim data blocks that were received during the data exchange session (operation 141). Any interim data blocks are assembled on a per patient and per patient medical device basis. For each patient and for each patient medical device, the patient management device 12 evaluates the entirety of the data received (operation 142). The data is evaluated for consistency and correctness, such as by performing checksum and error detection operations. Additionally, any redundant data blocks are deleted (operation 143) and a final data set is constructed (operation 144).

Figure 13:
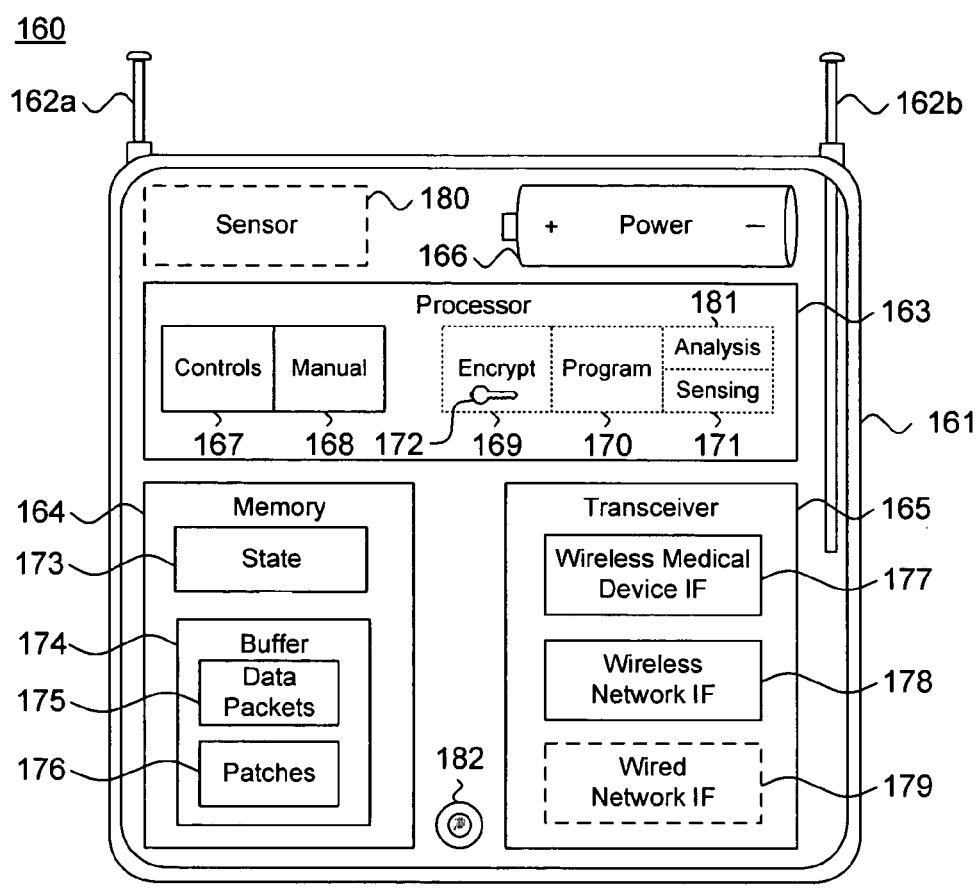
FIG. 13 is a functional block diagram showing, by way of example, an antenna point for use in the wireless medical device interrogation network of FIG. 2.

In a further embodiment, the patient management device 12, or other designated device, including any of the antenna points 21-24 functioning as intelligent antennas, as further described below with reference to FIG. 13, can analyze the data set (operation 145) and generate a local notification (operation 146), for instance, advising the patient 29 to promptly contact his or her caregiver. Other post-analysis actions are possible. Finally, the final data set is relayed to the centralized server 15, or other external system or data repository for further processing and analysis (operation 147).

Final Data Packet Assembly

Figure 12:
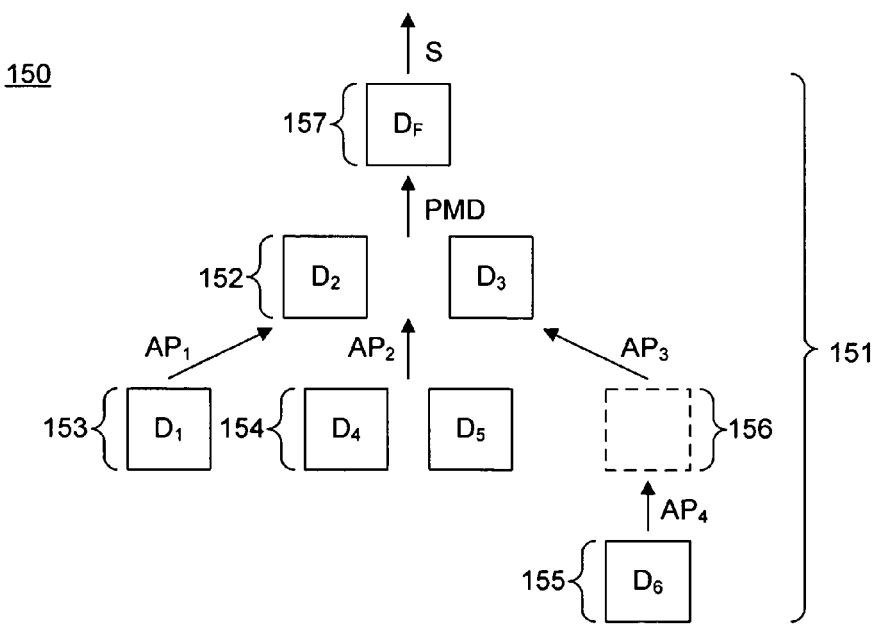
FIG. 12 is a tree diagram showing, by way of example, final data packet assembly.

The final data set collectively provided by the wireless medical device interrogation network 20 is a superset of the interim data received during the data exchange session. FIG. 12 is a tree diagram 150 showing, by way of example, final data packet assembly 151. Data block consolidation can be preformed hierarchically as a bottom-up data merge based on the network topology, or by any other methodology. Thus, the patient data 155 received by the fourth antenna point $AP_4$ is forwarded to the third antenna point $AP_3$, to which the fourth antenna point $AP_4$ is interconnected in relay. The patient data 153,154 respectively received by the first antenna point $AP_1$ and the second antenna point $AP_2$ are forwarded to the patient management device 12, which also receives patient data 156 forwarded from the third antenna point $AP_3$. The patient management device PMD consolidates the received patient data 153, 154, 156 with the patient data 152 that was directly received from a final data set 157, which is forwarded to the centralized server 15.

Antenna Point

Each antenna point 21-24 and the patient management device 12 serve as independent but interconnected interrogation points within wireless medical device interrogation networks 20. The antenna points 21-24 provide a cost savings by enabling the range of a patient management device 12 to be flexibly extended, which can be particularly helpful in environments in which the full interfacing and networking features of a patient management device 12 are not required at every interrogation point. Additionally, the antenna points 21-24 and patient management device 12 provide a network of interrogation zones formed into cells of wireless coverage with automatic handoff and recovery.

Antenna points 21-24 and patient management devices 12 share similar components for interfacing with patient medical devices. However, the antenna points 21-24 generally lack the general-purpose functionality and patient-operable user interface 13 of patient management devices 12 and need not include analysis or components for forwarding patient data to external systems or data repositories. FIG. 13 is a functional block diagram showing, by way of example, an antenna point 160 for use in the wireless medical device interrogation network 20 of FIG. 2. In one embodiment, each antenna point 160 executes a sequence of program or process steps, such as described above beginning with reference to FIG. 7, implemented, for instance, on a programmed digital computer or micro-programmable device.

Structurally, each antenna point 160 includes one or more antennas 162a-b, processor 163, memory 164, and transceiver 165. The antennas 162a-b can provide overlapping or discrete areas of wireless coverage, or be used in series to boost signal gain. The antenna point 160 includes a power supply 166, which can be self-contained, such as through rechargeable batteries, or through an external power source, typically provided through a standard wall outlet. Each antenna point 160 is contained in a housing 161, which can include an indicator light 161 or other indication that confirms operation.

The processor 163 includes a controls module 167 that controls standby, interrogation session, and hand-off operations. The controls module 167 conducts interrogation, during which patient data can be received from and, in a further embodiment, programming instructions sent to a selected patient medical device. The controls module 167 also manages hand-off operations by maintaining state 173 for data exchange sessions in a memory 164 and requesting the re-exchange of those interim data packets, which were only partially received upon an interruption of a data exchange session. The state 173 can include a sequence number for the last patient data block successfully received, although other types of state are possible. Patient data packets 175 and, in a further embodiment, programming instructions patches 176, are transiently stored in a buffer 174 also in the memory 164. In a further embodiment, the processor 163 includes a manual control module 168, which enables a patient 29 or attendant to manually activate and control the antenna point 160.

The transceiver 165 includes a wireless medical device interface 177 through which to communicate with patient medical devices during interrogation sessions. The wireless medical device interface 177 can pulse and modulate bidirectional transaction signal power to the lowest level necessary to successfully transact a wireless patient data exchange session, thereby preserving battery life on implantable patient medical devices. In one embodiment, the interrogation sessions occur over a Bluetooth-compliant, WiFi-compliant, WiMax-compliant, or proprietary wireless data communications network. Additionally, the transceiver 165 includes a wireless network interface 178, which enables the antenna point 160 to connect with other antenna points 21-24 and the patient medical device 12. The wireless network interface 178 can also operate over a Bluetooth-compliant, WiFi-compliant, WiMax-compliant, or proprietary wireless data communications network. In a further embodiment, the transceiver 165 can include a wired network interface 179, either in addition to or in lieu of the wireless network interface 178, to provide a hard-wired connection to other antenna points 21-24 and the patient medical device 12.

In further embodiments, the processor 163 can perform additional functions to provide an "intelligent" antenna. For instance, the processor 163 can include an encryption module 169, which encrypts and safeguards patient data exchanged with patient medical devices and over the wireless medical device interrogation network 20. The encryption module 169 can use, for instance, a secure key 172 based, for instance, on public key encryption or other forms of symmetric or asymmetric encryption, including the Advanced Encryption Standard (AES). The processor 163 can also include a programming module 170 to download patches 176 containing programming instructions to the patient medical devices. The processor 163 can further include a sensing module 171, which can be coupled to a sensor 180 built into or connected to the antenna point 160 to measure and record patient physiometry and other data. Finally, the processor 163 can include an analysis module 181, which can analyze the data set and generate a local notification. Other antenna point functionality is possible.

While the invention has been particularly shown and described as referenced to the embodiments thereof, those skilled in the art will understand that the foregoing and other changes in form and detail may be made therein without departing from the spirit and scope of the invention.

What is claimed is:

1. A system for operating a wireless medical device interrogation network, comprising:
   a plurality of interrogation points that each cover different zones of interrogation to transact data exchange sessions with a wireless medical device;
   a state chronicling a record of interim data packets exchanged during each data exchange session and accessible by each of the interrogation points, wherein the state provides a resumption point in the event that the data exchange session is interrupted;
   and at least one transceiver and one or more antenna at each interrogation point to support frequency agile switching between the interrogation points and the wireless medical device during a wireless data exchange session.

2. A system according to claim 1, further comprising:
   a controls module configured to request re-exchange with the wireless medical device of each such interim data packet partially received upon an interruption of the wireless data exchange session.

3. A system according to claim 1, further comprising:
   a centrally designated device configured to assemble the interim data packets into a final data packet upon successful completion of the wireless data exchange session; and to communicate the final data packet to a server.

4. A system according to claim 1, further comprising:
   a wireless medical device interrogation network environment, comprising at least one of:
      one such interrogation network interconnected with one patient having at least one wireless medical device;
      interfacing one such interrogation network interconnected with a plurality of patients who each have at least one wireless medical device;
      interfacing a plurality of the interrogation networks interconnected with one patient having at least one wireless medical device; and
      interfacing a plurality of the interrogation networks interconnected with a plurality of patients who each have at least one wireless medical device.

5. A system according to claim 4, further comprising:
   a unique identifier associated with the wireless medical device, wherein the unique identifier is included with each interim data packet for use in patient and wireless medical device identification.

6. A system according to claim 1, further comprising at least one of:
   a sensor configured to sense data comprising one or more of physiological measures, parametric data, and environmental parameters, which is stored into interim data packets;
   an encryption module configured to encrypt the interim data packets during the wireless data exchange session; and
   a programming module configured to program the wireless medical device through the wireless data exchange session.

7. A system according to claim 1, wherein the wireless data exchange session is initiated with the wireless medical device through one of polling, scheduling, and on-demand.

8. A system according to claim 1, wherein the interrogation points interface in at least one of a hub configuration and a relay configuration.

9. A system according to claim 1, wherein each interrogation point is selected from the group comprising a patient management device, advanced programmer, and antenna point.

10. A system according to claim 1, wherein the wireless medical device is selected from the group comprising an implantable sensor, implantable therapeutic device, external sensor, and external therapeutic device.

11. A method for operating a wireless medical device interrogation network, comprising:
    transacting data exchange sessions with a wireless medical device over a plurality of interrogation points that each cover different zones of interrogation;
    maintaining a state chronicling interim data packets exchanged during each data exchange session and accessible by each of the interrogation points, wherein the state provides a resumption point in the event that the data exchange session is interrupted; and
    supporting frequency agile switching between the interrogation points and the wireless medical device during a wireless data exchange session.

12. A method according to claim 11, further comprising:
    requesting re-exchange with the wireless medical device of each such interim data packet partially received upon an interruption of the wireless data exchange session.

13. A method according to claim 11, further comprising:
    assembling the interim data packets into a final data packet upon successful completion of the wireless data exchange session; and
    communicating the final data packet to a server.

14. A method according to claim 11, further comprising:
    configuring a wireless medical device interrogation network environment, comprising at least one of:

interfacing one such interrogation network to one patient having at least one wireless medical device;

interfacing one such interrogation network to a plurality of patients who each have at least one wireless medical device;

interfacing a plurality of the interrogation networks to one patient having at least one wireless medical device; and interfacing a plurality of the interrogation networks to a plurality of patients who each have at least one wireless medical device.

15. A method according to claim 14, further comprising:

associating a unique identifier with the wireless medical device; and including the unique identifier with each interim data packet for use in patient and wireless medical device identification.

16. A method according to claim 11, further comprising at least one of:

sensing data comprising one or more of physiological measures, parametric data, and environmental parameters, which is stored into interim data packets;

encrypting the interim data packets during the wireless data exchange session; and programming the wireless medical device through the wireless data exchange session.

17. A method according to claim 11, further comprising:

initiating the wireless data exchange session with the wireless medical device through one of polling, scheduling, and on-demand.

18. A method according to claim 11, further comprising:

interfacing the interrogation points in at least one of a hub configuration and a relay configuration.

19. A method according to claim 11, wherein each interrogation point is selected from the group comprising a patient management device, advanced programmer, and antenna point.

20. A method according to claim 11, wherein the wireless medical device is selected from the group comprising an implantable sensor, implantable therapeutic device, external sensor, and external therapeutic device.

21. A wireless antenna point for use in a medical device interrogation network, comprising:

a device interface to wirelessly connect to a medical device;

a buffer to stage data exchanged with the medical device;

a state to track the data last successfully exchanged, wherein the state comprises a sequence number for the last patient data block successfully retrieved; and a network interface to connect with one or more of other wireless antenna points and a patient management device; and an arbiter to designate one of the wireless antenna points upon interruption of an active connection between medical device and one such wireless antenna point.

22. A system according to claim 1 wherein the state further chronicles a resumption point in the data exchange session for use if the data exchange session is interrupted.

23. A method according to claim 11 further comprising re-designating an interrogation point if the data exchange session is interrupted.

24. A method according to claim 11 further comprising chronicling a resumption point in the data exchange session for use if the data exchange session is interrupted.

25. A system according to claim 1, wherein the data exchanged is cardiac data and wherein the wireless medical device is an implanted medical device.

* * * * *